United States Patent [19]

Fergason

[11] Patent Number: 4,765,719
[45] Date of Patent: Aug. 23, 1988

[54] OPTICAL PROTECTION USING SMECTIC LIQUID CRYSTAL

[76] Inventor: James L. Fergason, 92 Adam Way, Atherton, Calif. 94025

[21] Appl. No.: 10,748

[22] Filed: Feb. 4, 1987

[51] Int. Cl.$^4$ .............................................. G02F 1/13
[52] U.S. Cl. ................................. 350/350 S; 350/330; 350/347 V
[58] Field of Search ................ 350/330, 347 V, 350 S

[56] References Cited

U.S. PATENT DOCUMENTS

| 4,373,218 | 2/1983 | Schachar | 350/347 V X |
| 4,601,545 | 7/1986 | Kern | 350/332 X |

FOREIGN PATENT DOCUMENTS

| 2530039A | 1/1984 | France | |
| 2011640A | 7/1979 | United Kingdom | 350/334 |
| 2169417A | 7/1986 | United Kingdom | 350/334 |

Primary Examiner—Stanley D. Miller
Assistant Examiner—Richard F. Gallivan
Attorney, Agent, or Firm—Renner, Otto, Boisselle & Lyon

[57] ABSTRACT

Apparatus (10) for responding to incident electromagnetic radiation (16) to prevent direct transmission thereof when the magnitude of E-vector exceeds a predetermined value includes a first medium (12) through which incident electromagnetic radiation may be transmitted and smectic liquid crystal (14) positioned with respect to the first medium for responding to such E-vector to undergo Kerr effect in proportion to such E-vector so as to cooperate with such first medium to effect refraction of such electromagnetic radiation at an interface of the first medium and liquid crystal to prevent direct transmission of such radiation when the E-vector exceeds such predetermined magnitude. Smectic to nematic phase transition also may be used to prevent direct light transmission when incident radiation causes heating in the liquid crystal material.

A method for responding to incident electromagnetic radiation to prevent transmission when the E-vector of such radiation exceeds a predetermined magnitude for short pulses of such radiation includes receiving incident electromagnetic radiation, directing such incident electromagnetic radiation into a first medium through which incident electromagnetic radiation may be transmitted, using smectic liquid crystal positioned with respect to the first medium for responding to a characteristic of the incident electromagnetic radiation to cooperate with such first medium to effect refraction of such electromagnetic radiation at an interface of the first medium and the liquid crystal.

17 Claims, 4 Drawing Sheets

OPTICAL PROTECTION USING SMECTIC LIQUID CRYSTAL

TECHNICAL FIELD

This invention relates generally, as is indicated, to optical protection using smectic liquid crystal, and, more particularlay, to apparatus and method that uses smectic liquid crystal to respond to high intensity and/or highly coherent light for preventing transmission thereof.

BACKGROUND

Liquid crystal materials primarily are categorized as three types. These include smectic, nematic and cholesteric liquid crystal materials. Such materials have respective characteristic structural and operational properties. For example, some types of nematic liquid crystal material are anisotropic and birefringent. Moreover, some liquid crystal materials may have characteristics of one phase, say a smectic phase, at one temperature and a different phase, say a nematic phase, at a different temperature.

One exemplary use of the birefringent characteristics of nematic liquid crystal material in a containment medium in the past has been to effect controlled scattering of incident light. For instance, if the ordinary index of refraction and the extraordinary index of refraction of the liquid crystal are, respectively, the same as and different from the index of refraction of the medium, when the extraordinary index is encountered light will refract at the interface of the liquid crystal and medium and will scatter and when the ordinary index is encountered light will be transmitted without substantial refraction or scattering. Moreover, pleochroic dye has been used together with nematic liquid crystal material that is responsive to a prescribed input to dye, to filter or to absorb light as a function, for example, of structural characteristics of the liquid crystal material and dye.

Smectic liquid crystals are characterized by a structure which is generally laminar. Smectic liquid crystal materials have not been used until recently, and then in the limited construction of display devices and some memory devices. Smectic phase generally occurs at a temperature which is lower than the corresponding nematic or cholesteric phases that often are associated with optical applications. Earlier smectic liquid crystal materials were not used because the nature of the smectic phase makes it more difficult to align or to arrange the liquid crystal structure than the higher temperature phases.

The Kerr effect, more precisely the electrooptical Kerr effect, is a birefringence that is induced electrically. The basis of the Kerr effect theory is documented in various texts. Examples are *Light* by R. W. Ditchburn, Academic Press (London, 1976) and *Optics & Lasers* by Matt Young, Springer-Verlag (New York, 1984). The entire disclosures of such books are hereby incorporated by reference.

Light is a term by which reference is made to a form of electromagnetic radiation generally in a particular wavelength band or frequency range. In the context of the present invention light is used to refer to such electromagnetic radiation in the visible, ultra-violet and infrared ranges. Generally, the reference to light and to electromagnetic radiation herein means that electromagnetic radiation that will operate in accordance with the principles of the present invention.

BRIEF SUMMARY

Fundamentally, the present invention is intended to prevent the transmission of incident electromagnetic radiation as a function of a characteristic of such electromagnetic radiation. Preventing transmission may mean either preventing the direct transmission of incident light, e.g., by defocusing and/or by absorbing, and so on, as is described further below. Optical density or light density are referred to herein with respect to the intensity of light per unit area. For example, a beam of light having one cross sectional area may be spread to have a larger cross sectional area so as to include the same total quanta of light but to have a smaller intensity per unit area.

In a preferred embodiment and best mode of the invention such electromagnetic radiation is light, and, more specifically, coherent light, and such characteristic is the particular degree of coherence, intensity or both. Briefly, the invention relies on Kerr effect in a smectic liquid crystal material (preferably smectic-A liquid crystal material) to alter the index of refraction characteristic of such material as a function of the magnitude of the electric field vector of incident coherent light. The response to a large electric field vector is very fast; and the operative result of the altered index of refraction characteristic of the liquid crystal material is the presentation to the incident light of a refracting interface that can be used to defocus and/or to spread the incident light to avoid damage to that (e.g., the eyes of a person, equipment, etc.) positioned behind the invention relative to the incident light. The invention also may include features that rely on a smectic to nematic phase transition in response to increased temperature of the liquid crystal material as a result of high intensity also to create such refracting interface for preventing direct transmission of incident light.

The mentioned preventing of direct transmission of incident light may be, for example, the focusing of light to a point beyond the Rayleigh limit and/or the focusing and then appreciably spreading the light to achieve a relatively low light density at the area being protected by the invention.

Briefly, according to the invention an apparatus for responding to incident electromagnetic radiation includes a first medium through which incident electromagnetic radiation may be transmitted, and liquid crystal means positioned with respect to said first medium for responding to a characteristic of the incident electromagnetic radiation to cooperate with such first medium to effect refraction of such electromagnetic radiation at an interface of said first medium and said liquid crystal means.

According to an additional aspect, the above apparatus is further characterized in said first medium having an index of refraction, said liquid crystal means having first and second indices of refraction, the former being substantially the same as the index of refraction of said first medium and the latter being different thereby to effect such refraction, and said first medium having a shape and said first medium and said liquid crystal means being positioned relative to each other to establish a refractive interface when said liquid crystal means has such second index of refraction characteristic.

According to yet an additional aspect, the above apparatus is further characterized in said first medium having an index of refraction, said liquid crystal means having an alterable index of refraction characteristic, one being substantially the same as the index of refraction of said first medium and at least another being different thereby to effect such refraction, and said first medium being shaped and said first medium and liquid crystal means being positioned relative to each other to establish a refractive interface when the indices of refraction of said first medium and of said liquid crystal means are different, said liquid crystal means being operative according to Kerr effect to respond to the electric field vector of incident coherent light promptly as a function of the magnitude of such vector to assume such second index of refraction characteristic in a time frame that is on the order of about $10^{-10}$ second or faster, and said liquid crystal means being responsive to temperature to undergo a smectic to nematic phase transition, and said first medium and said liquid crystal means in such nematic phase having shape and index of refraction characteristics to effect scattering of incident light.

Another aspect relates to an apparatus including liquid crystal material operative to undergo Kerr effect in response to and proportionally to the intensity of incident light in excess of a predetermined magnitude, a further medium having a different index of refraction than the liquid crystal material when the latter is undergoing Kerr effect, said index of refraction of the liquid crystal material increasing in response to Kerr effect and being cooperative with said further medium to cause self focusing to defocus and/or to decollimate incident light.

According to another aspect of the invention, a method for responding to incident electromagnetic radiation includes receiving incident electromagnetic radiation, directing such incident electromagnetic radiation into a first medium through which incident electromagnetic radiation may be transmitted, and using liquid crystal means positioned with respect to said first medium for responding to a characteristic of the incident electromagnetic radiation to cooperate with such first medium to effect refraction of such electromagnetic radiation at an interface of said first medium and said liquid crystal means.

According to a further aspect, the above method further includes selection of the first medium to have an index of refraction, the liquid crystal means having alterable index of refraction, being substantially the same as the index of refraction of said first medium and another being different thereby to effect such refraction, and said first medium being shaped and said first medium and liquid crystal means being positioned relative to each other to establish a refractive interface when the indices of refraction thereof are different, said liquid crystal means being operative according to Kerr effect to respond to the electric field vector of incident coherent light, preferably coherent light, promptly as a function of the magnitude of such vector to assume such second index of refraction characteristic in a time frame that is on the order of about $10^{-10}$ second or faster, and said liquid crystal means being responsive to temperature to undergo a smectic to nematic phase transition, and said first medium and said liquid crystal means in such nematic phase having shape and index of refraction characteristics to effect scattering of incident light.

These and other objects, aspects, features, embodiments and advantages will become more apparent from the following detailed description of the invention.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DESCRIPTION OF THE PREFERRED EMBODIMENT

Figure 1:
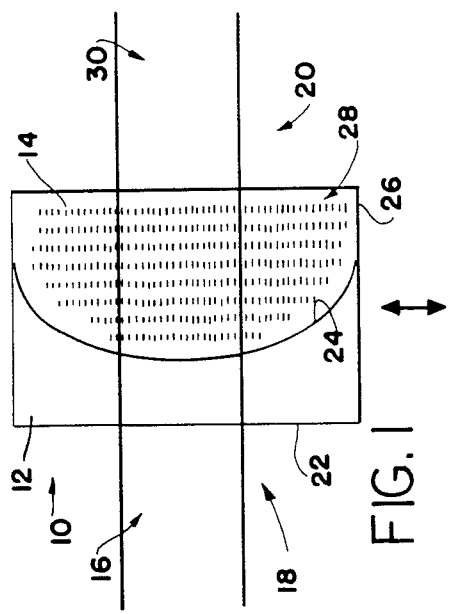
FIG. 1 is a schematic representation of the preferred embodiment of the present invention depicting incident collimated light being transmitted directly through the first medium and the liquid crystal material without refraction.
Figure 2:
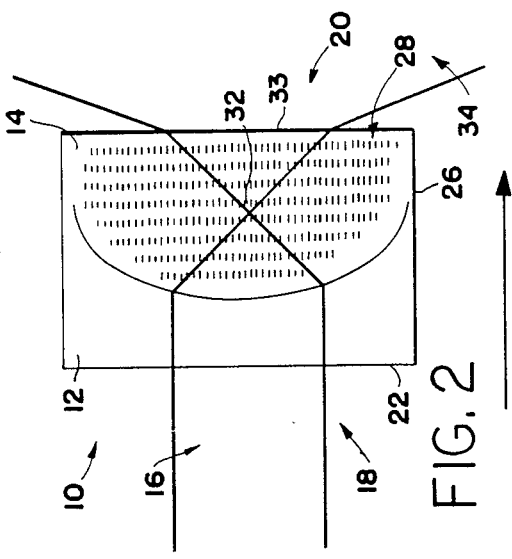
FIG. 2 is a schematic representation of the preferred embodiment of the present invention depicting high intensity and/or coherent collimated incident light being refracted at the interface of the first medium and the liquid crystal material to achieve self-focusing thereby preventing direct transmission of incident collimated light.

Referring, now, in detail to the drawings, wherein like reference numerals designate like parts in the several figures, and initially to FIGS. 1 and 2, an apparatus according to the present invention for transmitting light or for preventing transmission of light is designated 10.

The apparatus or device 10 includes a first medium 12 and a liquid crystal material 14. The device 10 is intended to permit the direct transmission of incident light 16 received at the incident side or input side 18 of the device when the degree of coherence of such incident light and/or the intensity of the incident light is/are less than a prescribed magnitude, e.g. less than a magnitude that may cause damage to an observer, equipment, etc. located on the protected side or output side 20 of the device. However, the device 10 is operative to prevent the direct transmission of incident light 16 to such output side 20 when, for example, such magnitude is exceeded.

In the illustrated embodiment, the first medium 12 may be an optically transparent material. Such material has a plane surface 22 at the input side 18, for example so that such surface ordinarily would not effect refraction of incident light, especially if such incident light is collimated and is received in a direction normal to such surface 22. The surface 22 may be other than plane, as will be appreciated, depending on the particular use of the device 10 while, of course, taking into consideration the indices of refraction of the first medium 12 and of the environment external of the surface 22, e.g. to the left as viewed in FIGS. 1 and 2. The first medium 12 also preferably has a refracting surface 24 that is intended to form an interface with the liquid crystal material 14. Intermediate materials may be placed between the refracting surface 24 and the liquid crystal material 14, if desired.

According to the preferred embodiment, such refracting surface 24 is curved so as to form a negative lens that would tend to focus light incident on an interface of the such refracting surface 24 and the liquid crystal material 14 when the indices of refraction thereof are different, as is represented in FIG. 2 in particular. The first medium 12 also may include a containing wall 26 to define a volume 28 within which the liquid crystal material 14 is contained. Alternatively, such volume 28 may be defined by means other than such a containing wall 26, as long as the liquid crystal material 14 is retained relative to the refracting surface 24 to accomplish refraction of light when desired. The material of which the first medium is made may be glass, a polymer, a plastic, a crystalline material, or other material that preferably is not affected by and does not affect the liquid crystal material 14 at the interface of the refracting surface 24 and the liquid crystal material and that has the desired optical transmission and index of refraction characteristics.

The liquid crystal material preferably is a material that operates as smectic liquid crystal material and, therefore, may be categorized as operationally smectic. Exemplary smectic or operationally smectic liquid crystal materials that may be used in accordance with the present invention include the following four materials, each of which is comprised of the stated propoertional recipe for making same. Abbreviations are used for space minimizing, as follows:

K-24 is 4-Cyano-4'-n-octylbiphenyl represented

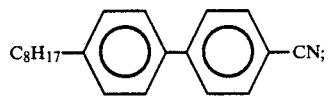

K-30 is

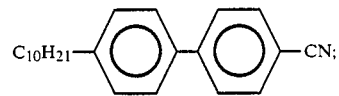

K-36 is 4-Cyano-4'-n-Dodecanylbiphenyl represented

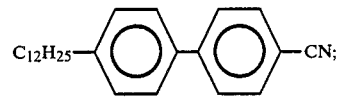

The foregoing three materials are sold by British Drug House (BDH).

2LI-1844 is nematic liquid crystal sold by E. Merck.

Exemplary operationally smectic materials useful in the invention are identified below. Each of such materials 1, 2, 3 or 4 may be used according to the invention.

Material 1 is a combination of the following ingredients in the indicated percentages by weight:

| K-24 | 13.9% |
| K-30 | 26.6% |
| K-36 | 29.5% |
| 2LI-1844 | 30.0% |

Material 2 is a combination of the following ingredients in the indicated percentages by weight:

| K-24 | 19.2% |
| K-30 | 38.4% |
| K-36 | 42.4% |

Material 3 is a combination of the following ingredients in the indicated percentages by weight:

| K-24 | 16.6% |
| K-30 | 33.2% |
| K-36 | 36.7% |
| 2LI-1844 | 13.4% |

Material 4 is a combination of the following ingredients in the indicated percentages by weight:

| K-24 | 17.1% |
| K-30 | 34.2% |
| K-36 | 37.6% |
| 2LI-1844 | 11.0% |

Operation of the device 10 according to the invention generally is, as follows. Ordinarily light 16 incident on surface 22 will enter the first medium 12 and be transmitted therethrough. If the degree of coherency and/or intensity of the incident light 16 is such that the electric field vector thereof is below a prescribed magnitude, the liquid crystal material 14 will have an index of refraction characteristic that is the same as the index of refraction of the first medium 12. Therefore, such incident light 16 will be transmitted directly through the device 10, as is represented at 30 in FIG. 1.

However, if the degree of coherency and/or intensity of the incident light 16 is such that the electric vector thereof exceeds a prescribed level, the liquid crystal material 14 will be caused, is described below, to have an index of refraction characteristic that is different than the index of refraction of the first medium 12. Therefore, the light will be refracted at the refracting surface 24 and accordingly will be prevented from directly passing through the device 10. More particularly, according to the preferred embodiment, such refracted light will be focused at a point 32, which preferably is in the liquid crystal material volume 28. Such focused light tends to spread beyond the point 32 and further to be refracted at the exit thereof from the liquid crystal material and back wall 33 of the device 10. Therefore, the density of the light 34 exiting the device 10 will be much lower than the incident light and will not damage that which is located at the output side 20 and is to be protected by the device 10.

The illustrations of FIGS. 1 and 2 only show a single relatively large refracting surface 24. The extent of self focusing will be a function of the degree of curvature of such surface and the difference between the indices of refraction of the first medium 12 and the liquid crystal material 14. The self focusing can be regulated by dividing up the area of the refracting surface 24 to obtain onlt the self focusing needed to provide the desired level of protection on the back side or output side 20 of the device 10. For example, the refracting surface 24 and the volume 28 may in effect be formed as a multiple lens array. Also, refraction of light exiting the device 10 at the back wall 33 may be determined as a function of the shape of the back wall and the relation of the indices of refraction of the back wall and the external medium 35 relative thereto, e.g., air.

Figure 3:
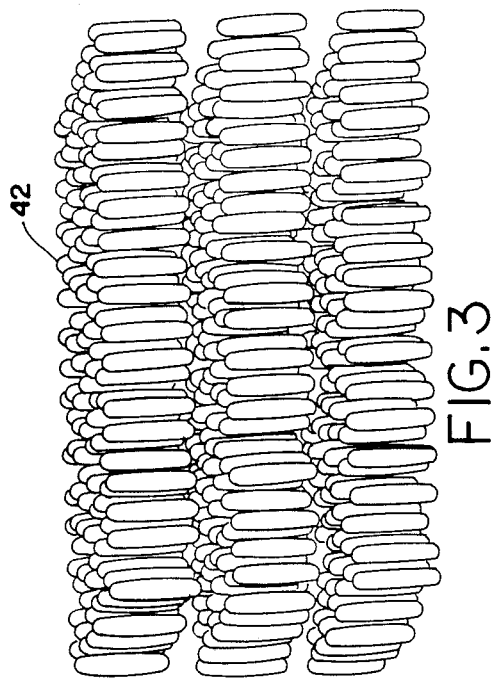
FIG. 3 is a schematic representation of the configuration of plural layers of cigar-shaped liquid crystal molecules of a smectic-A liquid crystal material.
Figure 4A:
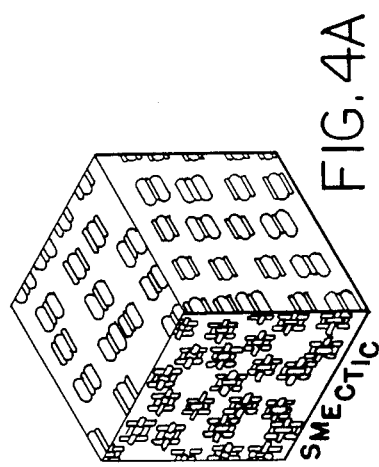
FIGS. 4A and 4B are schematic representations of the configurations of a smectic-A phase liquid crystal material showing the arrangement that would give rise to two-dimensional Kerr effect phenomena in accordance with the present invention.
Figure 4B:
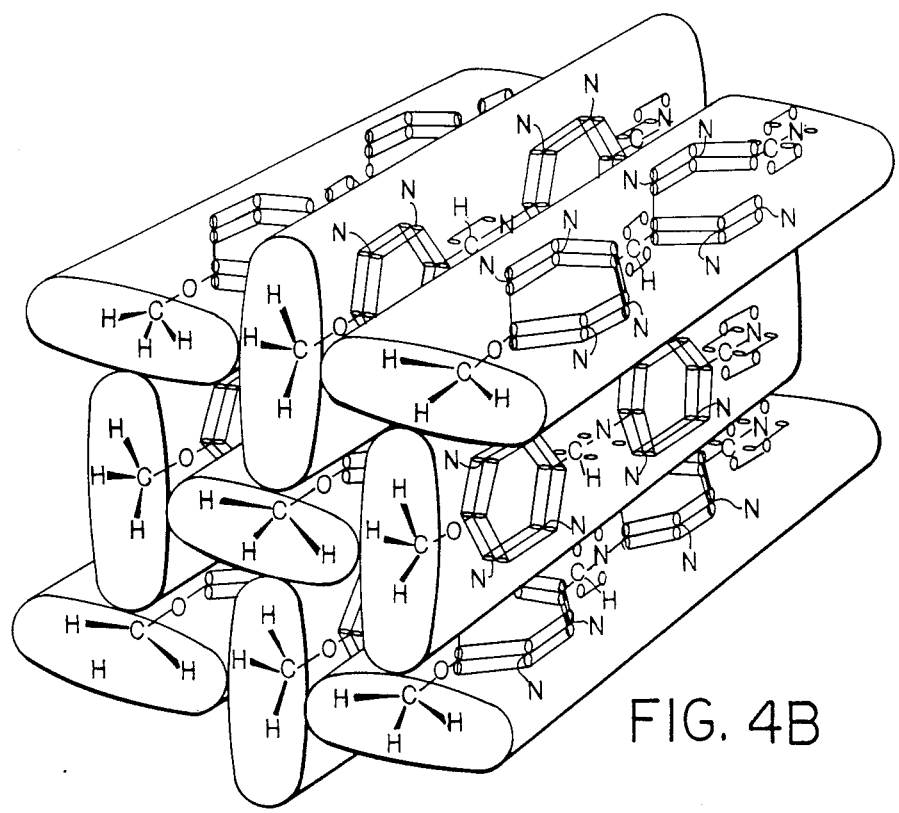

In FIG. 3, is illustrated a diagram of a smectic phase liquid crystal material. The liquid crystal molecules are free to move within a plane, but a crystal lattice-like structure occurs in the direction of the long axis of the molecule. This phase is often referred to as smectic A. Presently there are thousands of compounds which are known to give rise to a smectic A characteristic, many of which have smectic phases which are adapted to use within the temperature range from −20 degrees to +70 degrees C. In FIGS. 4A and 4B are illustrations of the configuration of molecules in a smectic phase liquid crystal material showing the arrangement of molecules that would give rise to two dimensional Kerr phenomena described herein.

The smectic A phase is generally found in a stage which can be best described as poly-crystalline, in that it is very seldom found naturally in a well-aligned state over large areas. By careful handling, this can be overcome and large areas of uniform liquid crystal can be obtained. In the case illustrated in FIG. 3, for example, there are planar layers which are able to flow over one another but which resist rupture or fracture. The optical characteristics of such material are those of a uniaxial crystal in which there is a single optical axis with the velocity of propagation of light a maximum along the optical axis.

Unlike a nematic liquid crystal in this characteristic direction, the smectic material is usually very transparent. The lack of transparency in a nematic liquid crystal is due to thermal oscillations in the direction of the optical axis. However, in a smectic liquid crystal, deformation which scatters light cannot occur readily since they would disrupt the layer spacing in the phase and therefore require energies much higher than that available from KT (i.e., thermal energies). Thus, only deformations of the layer which are possible with constant layer thickness can be made. These are generally referred to as splay deformations. These will give rise to scattering where the layers are curved.

Optical Frequency Field Effects

A property of smectic liquid crystal material, particularly smectic A material, is the two dimensional Kerr effect function or response. In the smectic phase, such smectic A liquid crystal material is a liquid in all characteristics in the dimensions at right angles to the layers, e.g. those represented in FIG. 3. If a strong E-vector (from a high intensity, highly coherent light, for example) is impressed on these layers at right angles in a time frame or at a sufficiently low energy density which prevents the long axis of the molecule from being affected, a change in the index of refraction would occur due to the nature of the molecules making up the smectic phase. By using electron dense materials, such as, derivatives of benzene and compounds such as thio ethers and thio esters, a phenomenon which is similar to the Kerr phenomenon in isotropic liquid occurs, i.e., the ability to undergo electronic transitions and to undergo alignment at low momentum leading to an increase of the index refraction. This increase in index refraction can be used to induce self-focusing and other phenomena which will break up the coherence of incident light 16, as is illustrated in FIG. 2 and, accordingly, will prevent direct transmission.

Thus, importantly, the present invention relates to a device 10, for example, that operates due to Kerr effect in such a way that when the E-vector of incident light exceeds a particular magnitude, the index of refraction of the liquid crystal material will increase and will be cooperative with another means, such as the first medium 12, to cause self focusing to defocus and/or to decollimate the incident light. As a result, the incident light will not pass straight through the device 10 and that which is on the output side 20 of the device 10 will be protected from damage that could be caused by high intensity light. The Kerr effect is relied on in the invention particularly to provide such protection from high intensity pulsed light beams, usually derived from pulsed lasers or the like; further the invention may be used to provide protection from more continuous high intensity incident light by reliance on scattering after a smectic to nematic transition and/or on absorption by pleochroic dye.

Exemplary operation of the device 10 relying on the two dimensional Kerr effect would be, as follows. As long as the incident light (or other electromagnetic radiation) has an electric field vector, e.g., due to coherence and/or due to intensity, that is below a prescribed magnitude that would cause a Kerr effect, the incident light 16 (FIG. 1) would be transmitted through the device 10, as the indices of refraction of the first medium 12 and of the liquid crystal material 14 preferably are matched or are at least about equal (most preferably are equal). However, if high intensity coherent light 16 were to impinge on the device 10, the electric field vector of that light being large enough to cause a two dimensional Kerr effect, the index of refraction of the liquid crystal material 14 would increase, and the self focusing depicted in FIG. 2 would occur. The actual degree of Kerr effect alteration of index of refraction of the liquid crystal 14, self focusing and, thus, decreasing of light density will be generally proportional to the magnitude of the mentioned electric field vector.

In one example of the present invention a Kerr effect response may cause a change in the index of refraction of the smectic A liquid crystal material from on the order of about 1.5 to an index of refraction that is about 1.56. Such a change is adequate to cause the lens or refraction effect illustrated in FIG. 2, for example, to obtain self focusing and protection of that on the output side 20 of the device 10 from damage due to a high intensity light source of short duration, such as a pulsed laser.

Since the device 10 uses smectic liquid crystal material 14, the larger index of refraction characteristic of the liquid crystal material occurring after undergoing the mentioned Kerr effect phenomenon, may tend to remain a characteristic of the liquid crystal material until it is specifically reset back to the original value. Such reset may be carried out by applying an appropriate electric field directly to the liquid crystal material 14 to cause a preferred alignment or orientation that results in the original index of refraction characteristic being presented the refracting surface 24 and incident light 16, as is illustrated in FIG. 1.

Kerr effect is a phenomenon that occurs extremely rapidly. Therefore, the described operation of increasing index of refraction and self focusing also will occur extremely rapidly. For example, the device 10 may respond to a light pulse 16 that has a duration on the order of $10^{-9}$ second or shorter. Preferably such pulse has a duration of $10^{-10}$ or shorter. If the duration of the incident light 16 is larger than, say $10^{-10}$ or $10^{-9}$ second, thermal effects will occur and local heating in the smectic A liquid crystal material may cause a smectic to nematic transition, as is discussed further below. Such thermal effects (for example heating) will tend to spread locally in the liquid crystal material when the duration of the incident light pulse is on the order of one microsecond or longer. The optical characteristics and response due to heating in the smectic A liquid crystal material, particularly when causing a smectic to nematic phase transition, are discussed below. Such characteristics may be used to increase the protection afforded by the device due to the above-described Kerr effect.

Other Optical Characteristics

In response to increased temperature the smectic A material 14 may undergo a smectic to nematic phase transition. Such increased temperature may be caused by a continuous incident light on the device 10, for example. Optical transmission characteristics of the nematic phase liquid crystal material may be a function of the structural alignment of the nematic liquid crystal and the resulting index of refraction characteristics thereof and/or alignment of pleochroic dye therein.

For example, the nematic liquid crystal material may be oriented either in a parallel aligned structure so as to permit transmission of light therethrough without distortion or substantially without distortion or the nematic liquid crystal material may be aligned in a way that causes scattering or distortion of incident light. The parallel aligned structure may be caused by application of an electric field to the liquid crystal material; the non-parallel structure may be caused somewhat naturally, e.g. due to interaction of the liquid crystal material at the interface thereof with a medium (such as the refracting surface 24) containing the same, e.g., tending to force a somewhat distorted structural alignment. The scattering mentioned may be due to different indices of refraction encountered by light at the mentioned interface or within the volume of liquid crystal material itself.

The mentioned scattering caused by the non-aligned nematic phase liquid crystal material also will have the desired effect of decreasing optical or light density so as to protect that which is beyond the output side 20 of the device 10. This may be used to enhance the protective operation due to Kerr effect in the device 10.

Figure 5:
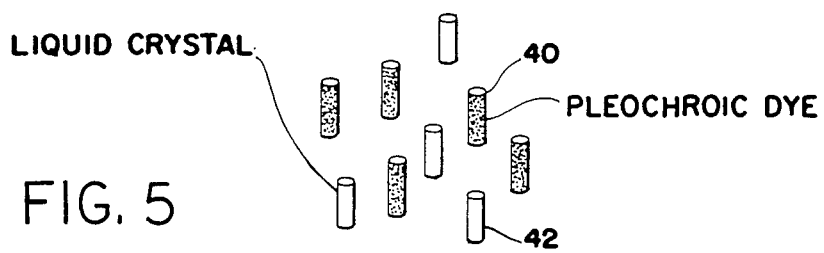
FIG. 5 is a schematic representation of alignment characteristics of pleochroic dye with respect to liquid crystal material.

A dye which has directional characteristics (often referred to as a pleochroic dye) can be incorporated in the smectic liquid. This generates differences in light absorption (as opposed to scattering or refracting of light) with direction. As is seen in FIG. 5, the pleochroic dye molecules 40 tend to align with respect to (e.g. in parallel with) the alignment of the smectic liquid crystal molecules 42. The use of pleochroic dye to absorb light, as is described herein, may further enhance the protective operation of the device 10 of the invention.

Figure 6:
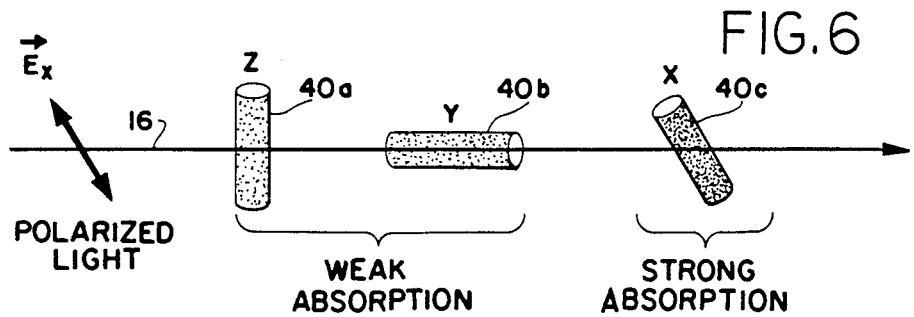
FIG. 6 is a schematic representation showing the relation of the polarization direction of light to the alignment orientation of pleochroic dye to achieve different levels of absorption by the dye.

In FIG. 6 the absorbing characteristics of a pleochroic dye molecule 40 as a function of the relation of the dye molecule 40 orientation relative to the electric field vector of an incident polarized light beam 16 is depicted. If the light beam 16 enters the liquid crystal and dye molecule 40a or 40b along the optical axis, almost no absorption occurs. However, if light 16 enters in which the electric vector is parallel to the pleochroic dye 40c or the optical axis, the absorption is very strong.

There is a group of smectic liquid crystals which will align in the presence of a strong electric field with the optical axis parallel to the electric field. These are referred to as smectic A's with positive dielectric anisotropy. Generally, a very high field is required to achieve such alignment due to planar configuration of large extent, e.g. as is illustrated in FIG. 3. However, if these materials are in a curved configuration and broken up in small volumes, the electric field can be substantially lowered and with a proper choice of materials, lose no clarity.

Figure 7:
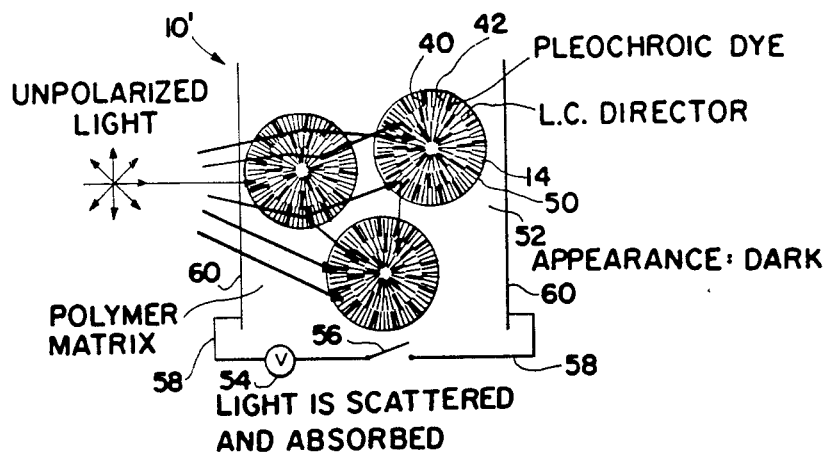
FIG. 7 is a schematic representation of a plurality of volumes of smectic liquid crystal material and pleochroic dye in an encapsulating medium, the liquid crystal structure and dye being in an orientation such that incident light is absorbed.
Figure 8:
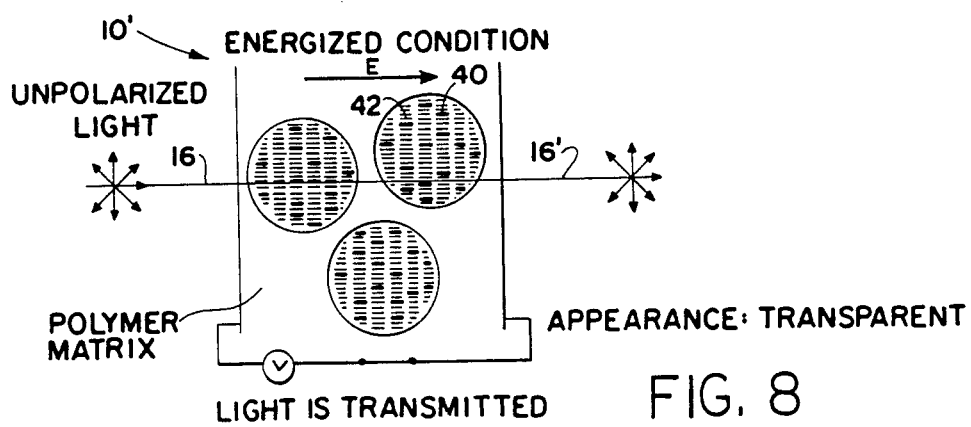
FIG. 8 is a schematic representation of a plurality of volumes of smectic liquid crystal material and pleochoric dye in an encapsulating medium similar to the illustration of FIG. 7 but with the liquid crystal structure and dye being subjected to an electric field to achieve an orientation such that incident light is transmitted.
Figure 9:
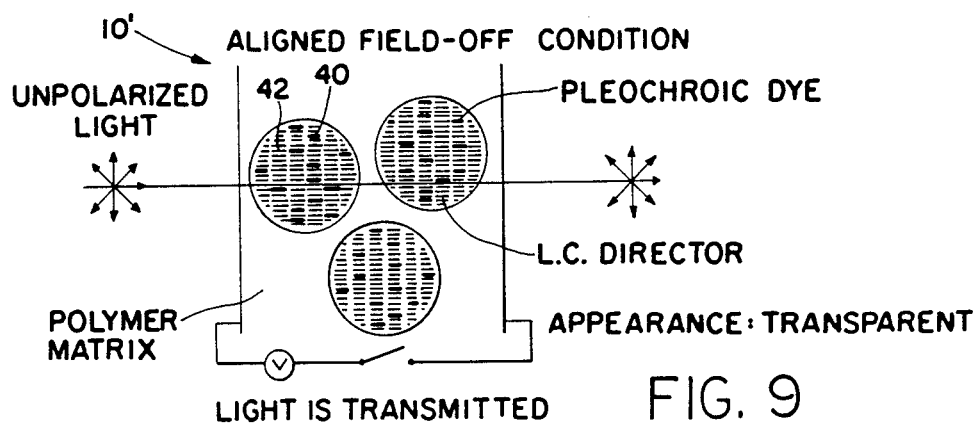
FIG. 9 is a schematic representation of a plurality of volumes of smectic liquid crystal material and pleochroic dye in an encapsulating medium similar to the illustration of FIG. 8 with the applied electric field removed and the liquid crystal structure and dye remaining in an orientation such that incident light is transmitted.

Briefly referring to FIGS. 7, 8 and 9, the confining of the smectic A liquid crystal material 14, for example, in plural volumes 50 of a containment medium 52, such as a polymer, epoxy, or other material matrix, is illustrated, e.g. as a device 10'. It will be appreciated that the principles referred to with respect to the plural volumes 50 may employed with the lens array or the like mentioned above with respect to the device 10.

Included in the volumes 50 of liquid crystal material 14 is pleochroic dye 40. The layered structure essentially in three dimensions of the volumes, which may be generally spherical, of the liquid crystal material is depicted in FIG. 7. The dye 40 shown in FIG. 7 follows the liquid crystal structure and tends to absorb a substantial amount of the incident light 16, regardless of whether such incident light is polarized or unpolarized.

In FIG. 8 an electric field is applied to the liquid crystal material 14 from an electric source 54 via a closed switch 56, circuit 58, and electrodes 60. Due to alignment of the liquid crystal structure and the dye structure with respect to the electric field, the incident light 16 will be transmitted, as is represented at 16' without distortion or change in clarity. A characteristic of smectic liquid crystal material is that it tends to retain its shape or structural orientation even after the electric field shown in FIG. 8 has been removed unless otherwise acted on by a force, energy, temperature, etc. As is seen in FIG. 9, such retention of orientation is depeicted; the liquid crystal structure and the dye structure remain parallel with each other and with the direction of light propagation therethrough. Distortion and absorption of incident light are minimal, and, accordingly, the incident light 16 is transmitted like light 16' mentioned above with respect to FIG. 8.

Clarity of light transmitted through the device 10' is immediately lost if the liquid crystal 14 in the absence of the field is induced to undergo a phase transition to the nematic liquid phase. Further, enhancing this effect in the Smectic A encapsulated material, the non-scattering state has a higher energy than the scattering state but will not change with available thermal energy isothermally. This gives rise to an enhanced non-linearity. Filters have been made which, in the presence of a high intensity light, can change their transmission characteristics by 50:1 or more in an extremely non-linear fashion. Since the change from smectic to nematic phase is first order (i.e. is substantially fully reversible) in many cases, this sharp transition allows good transmission to a certain intensity and then sharply above that intensity, the device becomes scattering. Thus, by properly adjusting the parameters of the device 10 or the device 10', an optical limiter can be made that works on the intensity of the incoming light.

Figure 10:
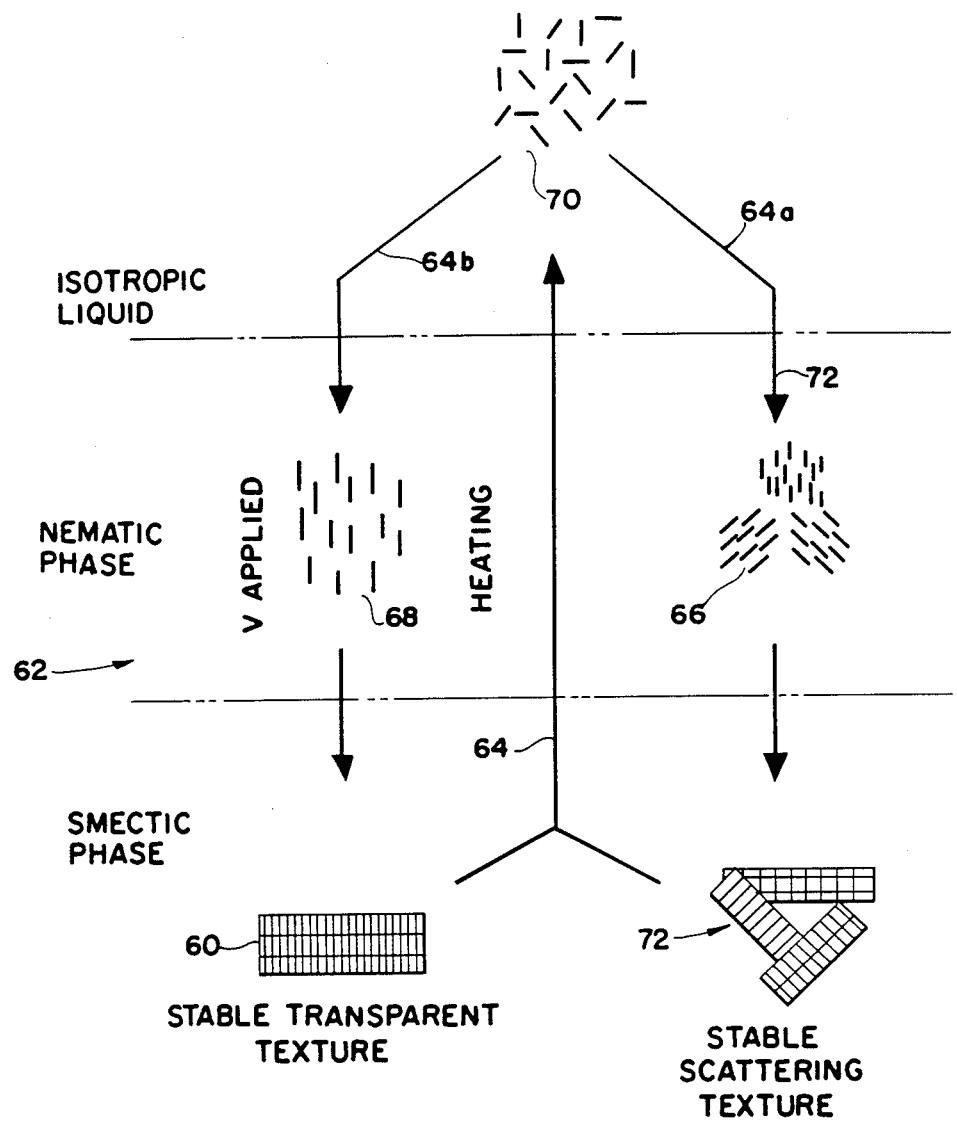
FIG. 10 is a schematic representation of the reversible phase transitions of liquid crystal used in accordance with the present invention.

Briefly referring to FIG. 10, the thermal pattern of performance of liquid crystal in the smectic A phase and nematic phase and as an isotropic liquid is shown. Specifically, a stable transparent smectic A texture shown at 60, e.g. representative of transmission characteristics of the device 10 of FIG. 1 or the transmission in the devices 10' of FIGS. 8 and 9. Upon heating to a prescribed temperature, e.g., say above about from 40 to 50 degrees C., transition to nematic phase occurs, as is represented at 62. The arrow 64 depicts such temperature elevation. In the nematic phase the liquid crystal material may scatter light if distorted from a linear structure, e.g. by interaction with the surface of a contanment medium, as is represented at 66; or if parallel aligned relative to an applied input, such as an electric field, the nematic phase liquid crystal material may transmit light, as is represented at 68. On the other hand, following the arrow 64 further up in FIG. 10, if the liquid crystal temperature were raised to that at which the liquid crystal material would become an isotropic material, as is represented at 70, the liquid crystal material would not cause significant scattering or alteration of light incident thereon.

Following the arrow 64a, when the isotropic liquid crystal material 70 cools, in the absence of an applied electric field it reassumes the nematic phase and will tend to be in randomly/distored alignment so as to scatter light, as is represented at 66. Such scattering will tend to occur due to the birefringence of the liquid crystal material and to the difference of the indices of refraction of the liquid crystal material and of the medium containing the same, e.g., the first medium 12 (FIG. 1) or the medium 52 (FIGS. 8 and 9). Interaction of such a medium is known to cause distortion of nematic liquid crystal structure to achieve the noted scattering. If the nematic phase liquid crystal material were in the scattering mode as is represented at 66, then when the temperature thereof is cooled further, the smectic A phase thereof also will be scattering, as is represented at 72 in FIG. 10. On the other hand, if the arrow 64b were followed, in the presence of electric field, the nematic phase liquid crystal material 68 would be in parallel alignment and would tend to transmit light with clarity. Applying electric field to the liquid crystal 66 also would result in the aligned structural orientation 68.

Importantly, upon further cooling of the nematic phase liquid crystal material 68 to a temperature at which the smectic A phase would result will produce the laminar layer structure 60 that is optically transmissive with minimal distortion, as is described above, particularly, with reference to the device 10 of FIGS. 1 and 2. The smectic A liquid crystal material 72 in the scattering configuration can be realigned to that structure represented at 60 in the transparent texture by increasing temperature of the smectic A material to achieve smectic to nematic transition; applying electric field to align the nematic phase achieving the aligned nematic phase 68; and finally allowing the material to cool back to the transparent smectic A texture 60. This realignment can occur in as short a time as a few milliseconds, depending upon the choice of liquid crystals.

SUMMARY OF INDUSTRIAL APPLICATION

It will be appreciated that the invention provides a way to protect humans and optical instrumentation from very intense light sources.

What is claimed is:

1. Apparatus for responding to incident electromagnetic radiation, comprising
   a first medium through which incident electromagnetic radiation may be transmitted;
   liquid crystal means positioned with respect to said first medium for responding to a characteristic of the incident electromagnetic radiation to cooperate with such first medium to effect refraction of such electromagnetic radiation at an interface of said first medium and said liquid crystal means.

2. The apparatus of claim 1, said first medium having an index of refraction, said liquid crystal means having first and second indices of refraction, the former being substantially the same as the index of refraction of said first medium and the latter being different thereby to effect such refraction, and said first medium having a shape and said first medium and said liquid crystal means being positioned relative to each other to establish a refractive interface when said liquid crystal means has such second index of refraction characteristic.

3. The apparatus of claim 2, said first medium including surface means for effecting a focusing of such electromagnetic radiation when said liquid crystal means has such second index of refraction characteristic.

4. The apparatus of claim 3, said liquid crystal means comprising smectic liquid crystal and said electromagnetic radiation comprising light.

5. The apparatus of claim 4, said electromagnetic radiation comprising coherent light, and said liquid crystal means being operative according to Kerr effect to respond to the electric field vector of such coherent light promptly to assume such second index of refraction characteristic.

6. The apparatus of claim 5, said liquid crystal means being operative according to Kerr effect to respond to the electric field vector of such coherent light promptly to assume such second index of refraction characteristic in a time frame that is on the order of faster than about $10^{-9}$ second.

7. The apparatus of claim 5, said liquid crystal means being operative according to Kerr effect to respond to the electric field vector of such coherent light promptly to assume such second index of refraction characteristic in a time frame that is on the order of faster than about $10^{-10}$ second.

8. The apparatus of claim 7, said liquid crystal means comprising smectic-A material.

9. The apparatus of claim 7, said liquid crystal means being responsive to temperature to undergo a smectic to nematic phase transition; and said liquid crystal means in such nematic phase having an index of refraction that is different from the index of refraction of said first medium thereby to effect scattering of incident.

10. The apparatus of claim 1, said first medium having an index of refraction, said liquid crystal means having first and second indices of refraction, the former being substantially the same as the index of refraction of said first medium and the latter being different thereby to effect such refraction, and said first medium being shaped and said first medium and liquid crystal means being positioned relative to each other to establish a refractive interface when said liquid crystal means has such second index of refraction characteristic, said liquid crystal means being operative according to Kerr effect to respond to the electric field vector of incident coherent light promptly as a function of the magnitude of such vector to assume such second index of refraction characteristic in a time frame that is on the order of faster than about $10^{-10}$ second, and said liquid crystal means being responsive to temperature to undergo a smectic to nematic phase transition, and said liquid crystal means in such nematic phase having an index of refraction that is different from the index of refraction of said first medium thereby to effect scattering of incident light.

11. The apparatus of claim 10, wherein such temperature effect is achieved as a function of intensity of incident light.

12. The apparatus of claim 11, further comprising pleochroic dye positioned relative to such liquid crystal means to absorb light as a function of liquid crystal structural orientation and corresponding dye orientation.

13. A method for responding to incident electromagnetic radiation, comprising
receiving incident electromagnetic radiation,
directing such incident electromagnetic radiation into a first medium through which incident electromagnetic radiation may be transmitted, and
using liquid crystal means positioned with respect to said first medium for responding to a characteristic of the incident electromagnetic radiation to cooperate with such first medium to effect refraction of such electromagnetic radiation at an interface of said first medium and said liquid crystal means.

14. The method of claim 13, said first medium having an index of refraction, said liquid crystal means having first and second indices of refraction, the former being substantially the same as the index of refraction of said first medium and the latter being different thereby to effect such refraction, and said first medium having a shape and said first medium and said liquid crystal means being positioned relative to each other to establish a refractive interface when said liquid crystal means has such second index of refraction characteristic.

15. The method of claim 14, further comprising using such liquid crystal means to monitor the intensity of such incident electromagnetic radiation, and undergoing a smectic to nematic phase transition in response to a prescribed increase in temperature to effect refraction of light.

16. The method of claim 13, said first medium having an index of refraction, said liquid crystal means having first and second indices of refraction, the former being substantially the same as the index of refraction of said first medium and the latter being different thereby to effect such refraction, and said first medium being shaped and said first medium and liquid crystal means being positioned relative to each other to establish a refractive interface when said liquid crystal means has such second index of refraction characteristic, said liquid crystal means being operative according to Kerr effect to respond to the electric field vector of incident coherent light promptly as a function of the magnitude of such vector to assume such second index of refraction characteristic in a time frame that is on the order of faster than about $10^{-10}$ second, and said liquid crystal means being responsive to temperature to undergo a smectic to nematic phase transition, and said liquid crystal means in such nematic phase having an index of refraction that is different from the index of refraction of said first medium thereby to effect scattering of incident light.

17. An apparatus, comprising liquid crystal material operative to undergo Kerr effect in response to and proportionally to the intensity of incident light in excess of a predetermined magnitude, a further medium having a different index of refraction than the liquid crystal material when the latter is undergoing Kerr effect, said index of refraction of the liquid crystal material increasing in response to Kerr effect and being cooperative with said further medium to cause self focusing to defocus and/or to decollimate incident light.

* * * * *

UNITED STATES PATENT AND TRADEMARK OFFICE
CERTIFICATE OF CORRECTION

PATENT NO. : 4,765,719
DATED : August 23, 1988
INVENTOR(S) : James L. Fergason

It is certified that error appears in the above-identified patent and that said Letters Patent is hereby corrected as shown below:

Column 1, line 8, change "particularlay" to --particularly--.

Column 7, line 23, change "onIt" to --only--.

Column 11, line 1, change "peicted;" to --picted;--.

Column 13, line 10, after "incident" add --light--.

Signed and Sealed this

Twenty-seventh Day of October, 1992

Attest:

DOUGLAS B. COMER

*Attesting Officer*   *Acting Commissioner of Patents and Trademarks*